United States Patent [19]

Cosma

[11] Patent Number: 4,686,977

[45] Date of Patent: Aug. 18, 1987

[54] TRACHEAL CANNULA

[76] Inventor: Frank Cosma, 15022 Alexandria St., San Leandro, Calif. 94579

[21] Appl. No.: 847,678

[22] Filed: Apr. 3, 1986

[51] Int. Cl.$^4$ ............................................. A61M 16/00
[52] U.S. Cl. ........................ 128/207.17; 128/DIG. 26; 128/912
[58] Field of Search ....................... 128/207.14–207.17, 128/200.26, DIG. 26, 912

[56] References Cited

U.S. PATENT DOCUMENTS

| | | | |
|---|---|---|---|
| 3,388,705 | 6/1968 | Grosshandler | 128/207.14 |
| 3,461,877 | 8/1969 | Morch | 128/207.14 |
| 3,693,624 | 9/1972 | Shiley et al. | 128/207.15 |
| 3,824,999 | 7/1974 | King | 128/207.17 |
| 3,978,854 | 9/1976 | Mills, Jr. | 128/204.26 |
| 4,033,353 | 7/1977 | La Rosa | 128/207.15 |
| 4,235,229 | 11/1980 | Ranford et al. | 128/207.17 |

*Primary Examiner*—Henry J. Recla
*Attorney, Agent, or Firm*—Linval B. Castle

[57] ABSTRACT

A tracheal cannula in which the cannula tube is pivotally coupled to its throat plate by a spherical ball formed at the external end of the tube and an engaging socket formed in the throat plate.

2 Claims, 4 Drawing Figures

TRACHEAL CANNULA

BRIEF SUMMARY OF THE INVENTION

This invention relates generally to tracheal cannulae and in particularly to a tracheal cannula which is coupled through a ball and socket to its supporting throat plate.

Tracheal cannulae are extensively used as a result of accidents or surgery that result in the blocking of the air passage to the lungs. The traceal cannula is a tube that is inserted through an opening in the patient's throat and into a similar opening made in the trachea leading directly to the lungs and enables normal breathing in emergency situations. Tracheal cannulae for more permanent use are curved plastic tubular members rigidly attached at one end to a throat plate which may be secured to the patient by a neck band or the like.

During normal daytime use the cannula with attached neck plate is not particularly uncomfortable to the patient if he does not turn his head excessively. But excessive head rotation and normal twisting during sleeping results in unbearable pain because the cannula is rigidly attached to the throat plate tied to the patient's neck and the cannula thus twists within the neck and trachea as the neck plate is similarly twisted. Tracheal cannula movement during sleeping has often resulted in internal chafing, bleeding and a bloody congestion in the lungs.

This invention is for a tracheal cannula which eliminates the above patient discomfort and which cannot become twisted.

Briefly described, the improved tracheal cannula is not rigidly connected to its throat plate but is coupled thereto by a ball and socket connection which permits the tube to move independently of the movement and position of the throat plate tied to the patients neck.

BRIEF DESCRIPTION OF THE DRAWINGS

In the drawings which illustrate the preferred embodiment of the invention.

DETAILED DESCRIPTION OF THE PREFERRED EMBODIMENT

Figure 1:
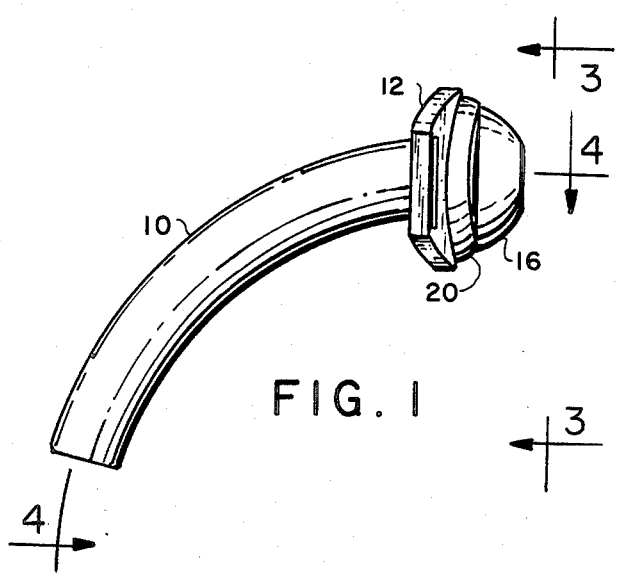
FIG. 1 is a side elevational view of the tracheal cannula.
Figure 2:
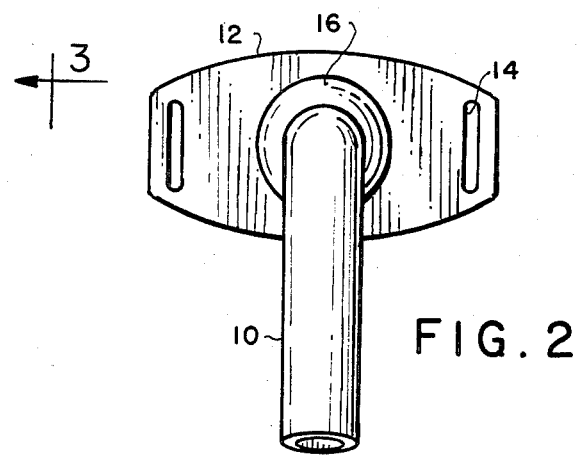
FIG. 2 is a rear elevational view thereof.
Figure 3:
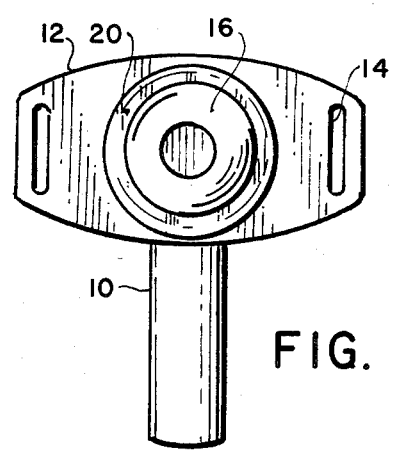
FIG. 3 is a front elevational view thereof.

As shown in FIG. 1, the tracheal cannula includes an arcuate tube 10 which is designed to enter a opening at the throat of a patient and into the trachea to permit free passage of air to and from the patient's lungs. As with all such cannulae and as better shown in FIGS. 2 and 3, the tube 10 is connected to a throat plate 12 provided with end slots 14 to receive a ribbon that is tied around the patient's neck to secure the cannula and prevent accidental removal from the trachea.

As discussed above, a rigid connection between cannula tube 10 and throat plate 12 results in great discomfort and possible chafing and bleeding.

Figure 4:
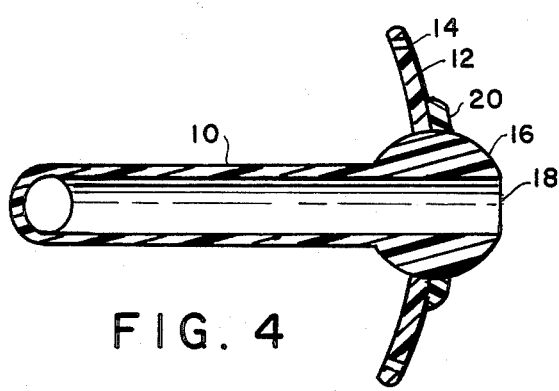
FIG. 4 is a sectional plan view taken along the lines 4—4 of FIG. 1.

As best shown in the sectional view of FIG. 4, the improved cannula provides a loose coupling between the tube 10 and throat plate 12 so that the throat plate serves only to maintain the cannula against the patient's throat and cannot affect the positioning of the tube 10 in the trachea. The loose coupling between tube 10 and throat plate 12 is provided by a ball and socket coupling in which a spherical ball 16 is formed at the exterior end 18 of the cannula tube 10. The throat plate is formed with a circular opening having a diameter slightly less than the diameter of the spherical ball 16. The frontal edge of the opening is chamfered to receive and retain the ball 16 and a retaining ring 20 with a similar circular opening and chamfer is cemented or otherwise connected over the ball 16 to the face of the throat plate 12. The facing chamfered openings in the throat plate and retaining ring thus provide the socket in the connection between the cannula throat plate and retaining ring and permit the cannula to rotate and to freely pivot vertically or horizontally in the throat plate socket. Thus, the positioning of the cannula in the trachea is freely adjustable and is not controlled or affected by the throat plate and any twisting or turning thereof.

Having thus described my improved tracheal cannula, what I claim is:

1. A tracheal cannula comprising:
   an arcuate cannula tube having a first end for entering the trachea of a patient and a second end extending outward from the throat area of the patient;
   a throat plate coupled to the second end of said cannula tube and securable to said throat area, the second end of said cannula tube being formed with a spherical ball and wherein said throat plate is formed with a ball socket engaging said spherical ball whereby the coupling between said throat plate and said second end permits rotation of said cannula tube and free horizontal and vertical pivoting thereof with respect to said throat plate.

2. The tracheal cannula claimed in claim 1 wherein said ball engaging socket if formed by a chamfered hole in said throat plate and a retaining ring having a similarly chamfered hole therein facing and attached to said throat plate and engaging the spherical ball at the second end of said cannula tube.

* * * * *